(12) United States Patent
Fang

(10) Patent No.: US 8,456,417 B2
(45) Date of Patent: Jun. 4, 2013

(54) USER INTERFACE FOR CONFIGURING IMAGE PRESENTATION

(75) Inventor: Irene Fang, Barrington, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 581 days.

(21) Appl. No.: 12/785,612

(22) Filed: May 24, 2010

(65) Prior Publication Data

US 2011/0063209 A1  Mar. 17, 2011

Related U.S. Application Data

(60) Provisional application No. 61/242,452, filed on Sep. 15, 2009.

(51) Int. Cl.
| | |
|---|---|
| *G09G 5/00* | (2006.01) |
| *G09G 5/02* | (2006.01) |
| *G06F 3/00* | (2006.01) |
| *G06F 3/048* | (2006.01) |
| *A61B 5/00* | (2006.01) |
| *H04N 7/00* | (2011.01) |
| *H04N 5/57* | (2006.01) |
| *H04N 1/46* | (2006.01) |
| *G03F 3/08* | (2006.01) |
| *G06K 9/00* | (2006.01) |
| *G06K 9/40* | (2006.01) |
| *G06K 9/32* | (2006.01) |

(52) U.S. Cl.
USPC ........... 345/157; 345/594; 345/606; 345/619; 345/653; 345/589; 348/552; 348/569; 348/673; 348/686; 348/687; 358/519; 358/525; 358/530; 382/167; 382/254; 382/274; 382/276; 382/296; 715/700; 715/722; 715/764; 715/856

(58) Field of Classification Search
USPC ................. 345/418–419, 581–594, 600–601, 345/606, 629–630, 617–619, 650, 653–659, 345/156–157, 168; 348/552–553, 557, 563–569, 348/571, 671, 673, 686, 687; 358/518–520, 358/525, 530, 448, 452–453; 382/154, 162, 382/167, 254, 266, 274, 276, 283, 296–297, 382/300, 307; 715/273, 275, 700, 722, 754, 715/763–764, 765, 856–857
See application file for complete search history.

(56) References Cited

U.S. PATENT DOCUMENTS

| | | | | |
|---|---|---|---|---|
| 5,113,517 A | * | 5/1992 | Beard et al. | ...................... 703/23 |
| 5,153,577 A | * | 10/1992 | Mackey et al. | ............... 345/639 |
| 5,570,108 A | | 10/1996 | McLaughlin et al. | |

(Continued)

*Primary Examiner* — Wesner Sajous
(74) *Attorney, Agent, or Firm* — Alexander J Burke

(57) ABSTRACT

A user interface system determines image display presentation characteristics using a displayed image parameter selection control providing image parameter selection data, responsive to the received cursor command data. The displayed image parameter selection control includes a shape having an origin and one or more different sectors associated with one or more corresponding different sets of parameters determining image color or grayscale characteristics and a linear element lying along a line from the origin to a perimeter of the shape and being rotatable about the origin, (a) within a sector to select a value within a range of values determining a first image display characteristic and (b) between sectors to select one of the different sets of parameters determining image color or grayscale characteristics. A display processor initiates display of an image having display presentation characteristics determined by the image parameter selection data.

20 Claims, 10 Drawing Sheets

U.S. PATENT DOCUMENTS

| | | | |
|---|---|---|---|
| 5,734,915 A * | 3/1998 | Roewer | 715/202 |
| 5,739,809 A | 4/1998 | McLaughlin et al. | |
| 6,337,692 B1 * | 1/2002 | Rai et al. | 345/594 |
| 6,999,068 B2 | 2/2006 | Sobol | |
| 7,428,018 B2 | 9/2008 | Kim et al. | |
| 2003/0112280 A1 * | 6/2003 | Driskell | 345/835 |
| 2004/0165113 A1 | 8/2004 | Kim et al. | |
| 2006/0284861 A1 | 12/2006 | Choi | |
| 2007/0120576 A1 * | 5/2007 | Ford et al. | 326/41 |
| 2008/0163114 A1 | 7/2008 | Choi et al. | |
| 2009/0201310 A1 | 8/2009 | Weiss | |
| 2012/0113000 A1 * | 5/2012 | Chao et al. | 345/157 |

* cited by examiner

FIGURE 3
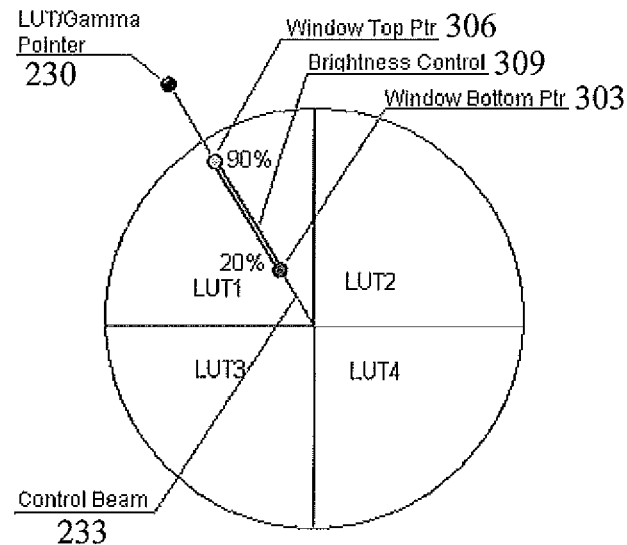
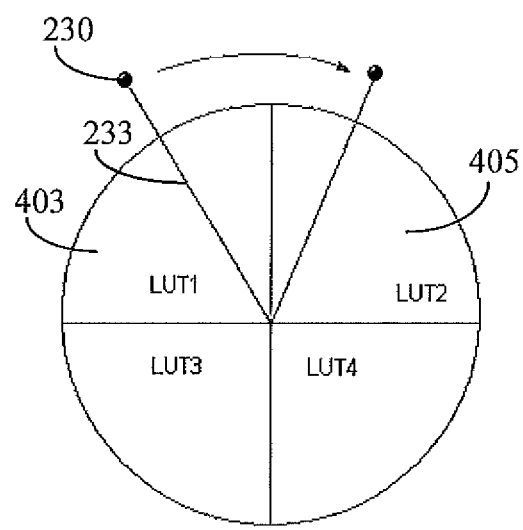
FIGURE 4

FIGURE 5
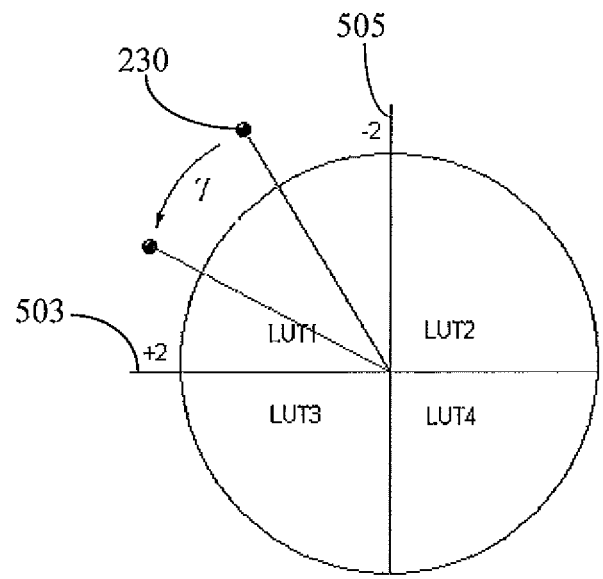
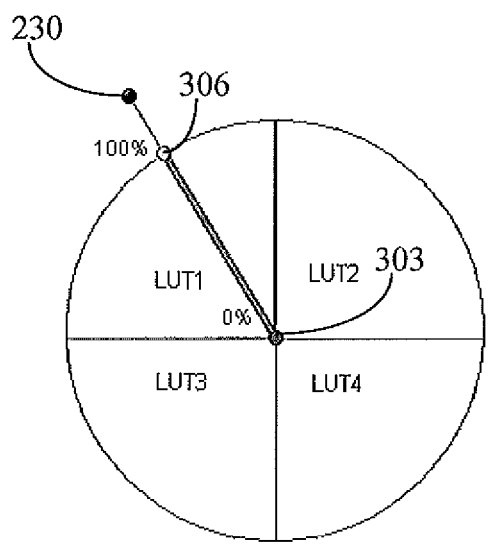
FIGURE 6

FIGURE 7
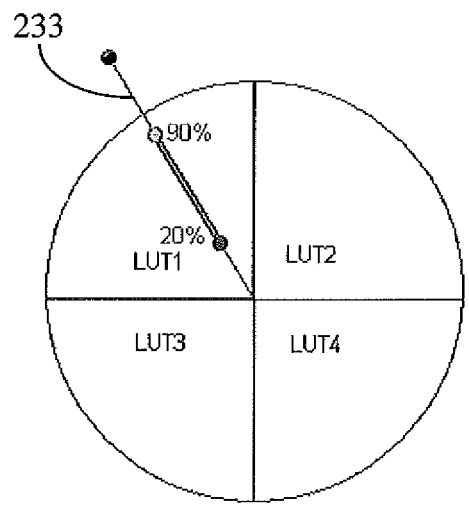
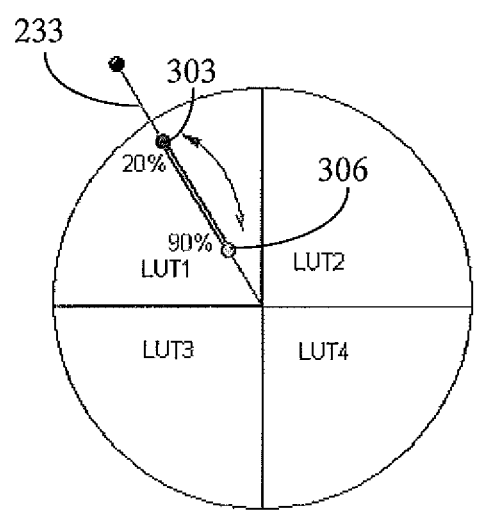
FIGURE 8

FIGURE 9
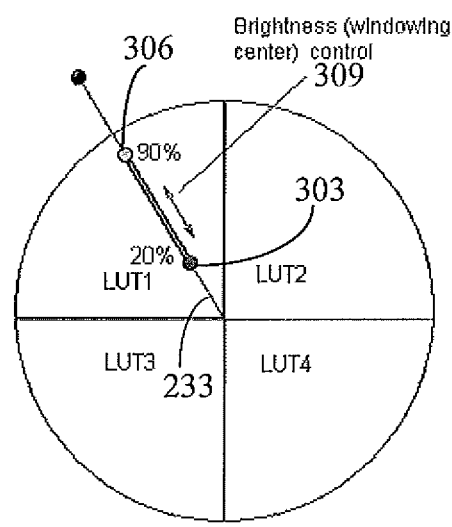
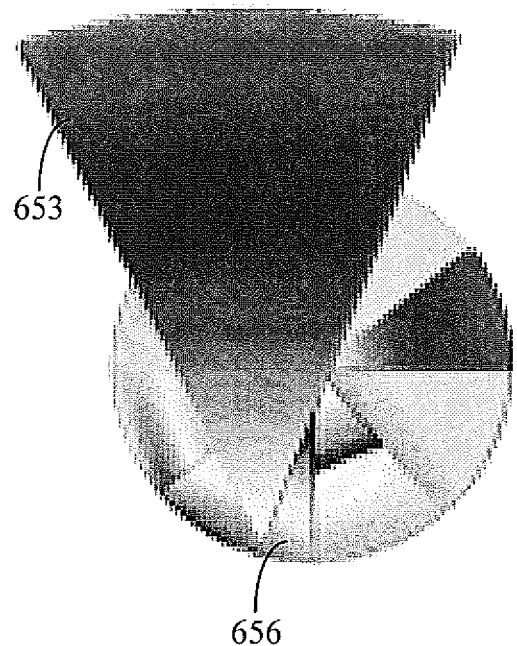
FIGURE 10

FIGURE 12
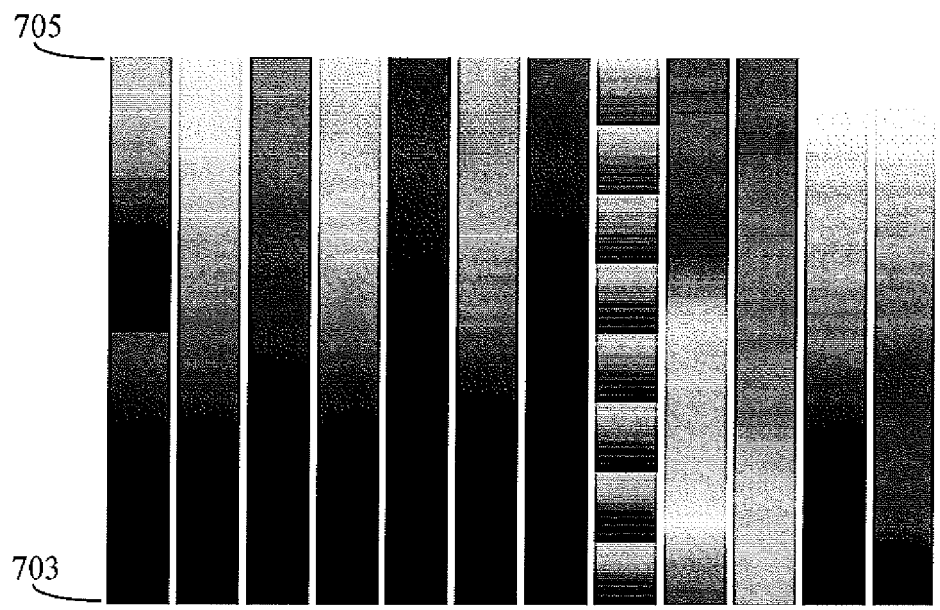
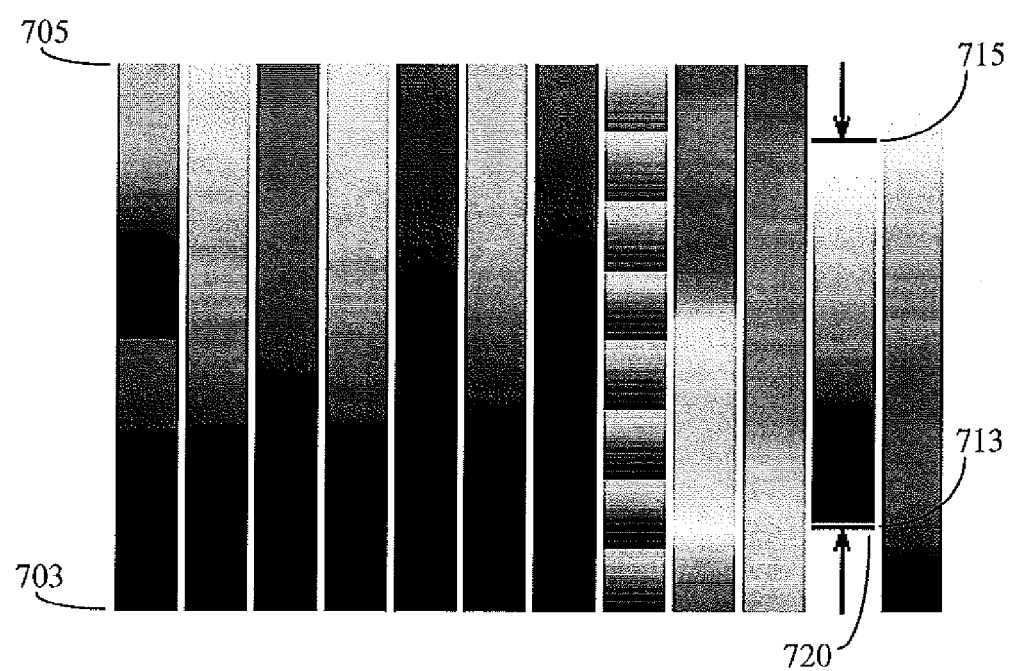
FIGURE 13

USER INTERFACE FOR CONFIGURING IMAGE PRESENTATION

This is a non-provisional application of provisional application Ser. No. 61/242,452 filed 15 Sep. 2009, by I. Fang.

FIELD OF THE INVENTION

This invention concerns a user interface system for determining image display presentation characteristics comprising a displayed image parameter selection control enabling a user to select a value within a range of values determining a first image display characteristic and enabling a user to select different sets of parameters determining image color or grayscale characteristics.

BACKGROUND OF THE INVENTION

There are different ways to manipulate color attributes in a digitally represented medical image, for example, when it is displayed on a computer. In known medical imaging applications, to adjust these parameters, a user typically needs to select, a color look up table (LUT) from a predefined list and a desired contrast by adjusting a top and bottom contrast value using a LUT user interface representation (such as a gradient bar LUT control). A user adjusts image brightness by moving a windowing position in the LUT control and changes a gamma value via some kind of context menu from the LUT control. Known systems employ multiple user interface controls involving burdensome, time consuming navigation for selecting image color attributes. A system according to invention principles addresses this deficiency and related problems.

SUMMARY OF THE INVENTION

A medical image presentation user interface provides multiple pre-defined color lookup tables (LUTs), each represented by a displayed gradient of color or gray scale shades, fitted in a pie slice in a pinwheel diagram, for example. A user interface system for determining image display presentation characteristics, comprises a cursor control device for receiving command data related to a displayed cursor in response to user physical interaction with the device. A displayed image parameter selection control provides image parameter selection data, responsive to the received command data. The displayed image parameter selection control includes a shape having an origin and one or more different sectors associated with one or more corresponding different sets of parameters determining image color or grayscale characteristics and a linear element lying along a line from the origin to a perimeter of the shape and being rotatable about the origin, (a) within a sector to select at least one value within a corresponding range of values determining a group of image display characteristics and (b) between sectors to select one of the different sets of parameters determining image color or grayscale characteristics. A display processor initiates display of an image having display presentation characteristics determined by the image parameter selection data.

BRIEF DESCRIPTION OF THE DRAWING

FIG. 3 illustrates image parameter selection control legends, according to invention principles.

FIG. 4 illustrates changing a color lookup table using an image parameter selection control, according to invention principles.

FIG. 5 illustrates adjusting gamma using an image parameter selection control, according to invention principles.

FIG. 6 illustrates adjusting contrast and brightness related Window Level Initial value Positions using an image parameter selection control, according to invention principles.

FIG. 7 illustrates adjusting contrast and brightness related Window Top and Bottom values within a color lookup table using an image parameter selection control, according to invention principles.

FIG. 8 illustrates inverting a color lookup table using an image parameter selection control, according to invention principles.

FIG. 9 illustrates adjusting brightness using an image parameter selection control, according to invention principles.

FIG. 10 illustrates zooming a color lookup table sector of an image parameter selection control, according to invention principles.

FIGS. 12 and 13 show vertical color lookup tables instead of circular shape based color lookup tables, according to invention principles.

DETAILED DESCRIPTION OF THE INVENTION

A system according to invention principles provides a user friendly user interface, i.e. a dialog box or a floating modeless window. In one embodiment, the interface presents a pinwheel graph associated with one or more pre-determined color lookup tables. The system enables color lookup table (LUT) selection, adjustment of image contrast, brightness and gamma factor of a medical image using a single image parameter selection control by moving (e.g., dragging) elements of the control. The single image parameter selection control also enables inversion of a color lookup table. The system reduces the layers and complexity of user interfaces involved and simplifies user navigation in adjusting medical image presentation attributes (e.g., color, brightness, contrast, gamma, and invert state), while optimizing user visual feedback. The user interface depicts multiple image presentation attributes, (color and gray scale look up table, image brightness and contrast and gamma, for example) in a single pinwheel (or other format) graphical element, allowing a user to visualize and modify settings in a single glance. The system plugs into image review and manipulation applications.

Figure 1:
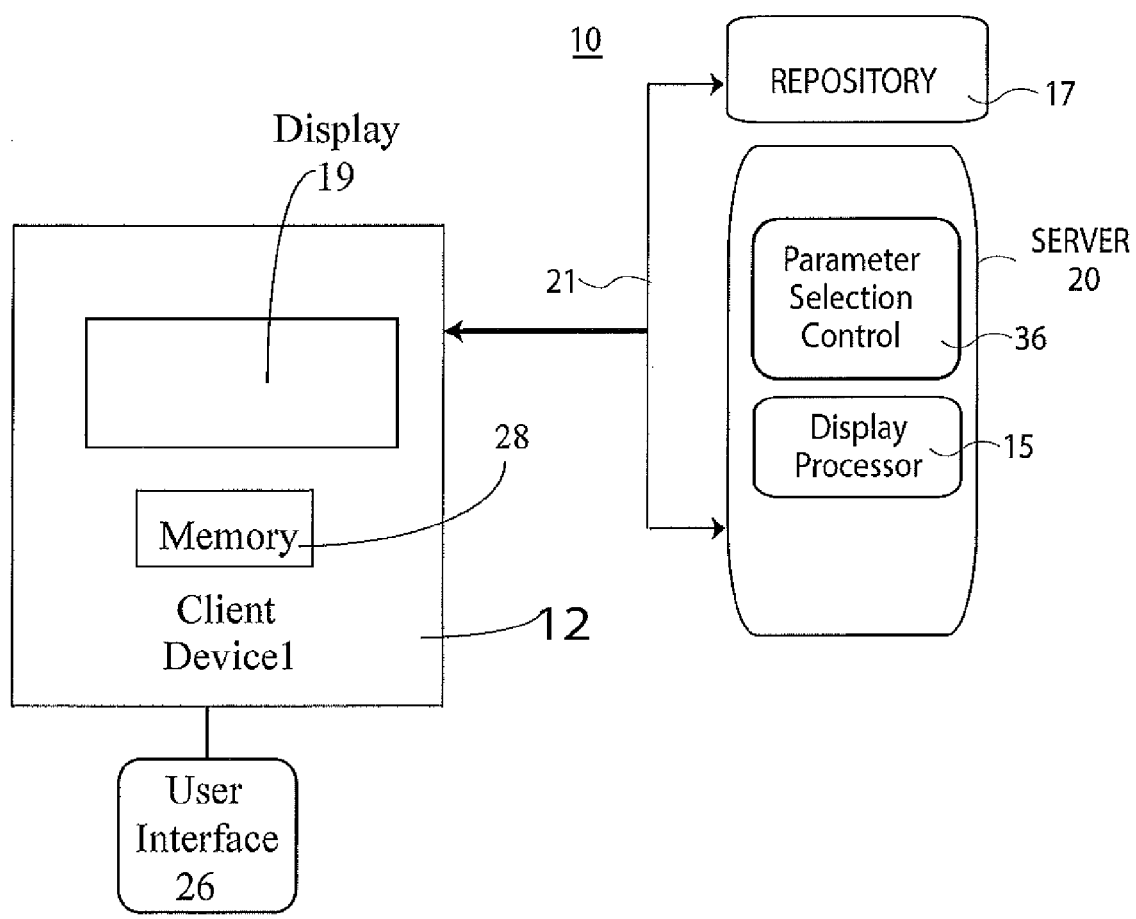
FIG. 1 shows a user interface system for determining image display presentation characteristics, according to invention principles.

FIG. 1 shows a user interface system 10 for determining image display presentation characteristics. System 10 includes one or more processing devices (e.g., computers, workstations or portable devices such as notebooks, Personal Digital Assistants, phones) 12 that individually include a user interface (e.g., a cursor) control device 26 such as a keyboard, mouse, touchscreen, voice data entry and interpretation device, at least one display monitor 19 and memory 28. System 10 also includes at least one repository 17 and server 20 intercommunicating via network 21. At least one repository 17 stores color look up table, image brightness and contrast and gamma parameters and data representing image menus including an image parameter selection control as well as medical image studies for multiple patients in DICOM compatible (or other) data format. A medical image study individually includes multiple image series of a patient anatomical portion which in turn individually include multiple images.

Server 20 includes display processor 15 and image parameter selection control 36. Display processor 15 provides data representing display images comprising a Graphical User Interface (GUI) for presentation on at least one display 19 of processing device 12 in response to user commands entered using device 26. In alternative arrangements, one or more of the units in server 20 may be located in device 12 or in another device connected to network 21. Cursor control device 26 receives command data related to a displayed cursor in response to user physical interaction with the device. Displayed image parameter selection control 36 provides image parameter selection data, responsive to the received command data. The image parameter selection control comprises, a shape having an origin and one or more different sectors associated with one or more corresponding different sets of parameters determining image color or grayscale characteristics and a linear element. The linear element lies along a line from the origin to a perimeter of the shape and is rotatable about the origin, (a) within a sector to select at least one value within a corresponding range of values determining a group of image display characteristic and (b) between sectors to select one of the different sets of parameters corresponding to the different sectors and determining image color or grayscale characteristics. Display processor 15 initiates display of an image having display presentation characteristics determined by the image parameter selection data.

Figure 2:
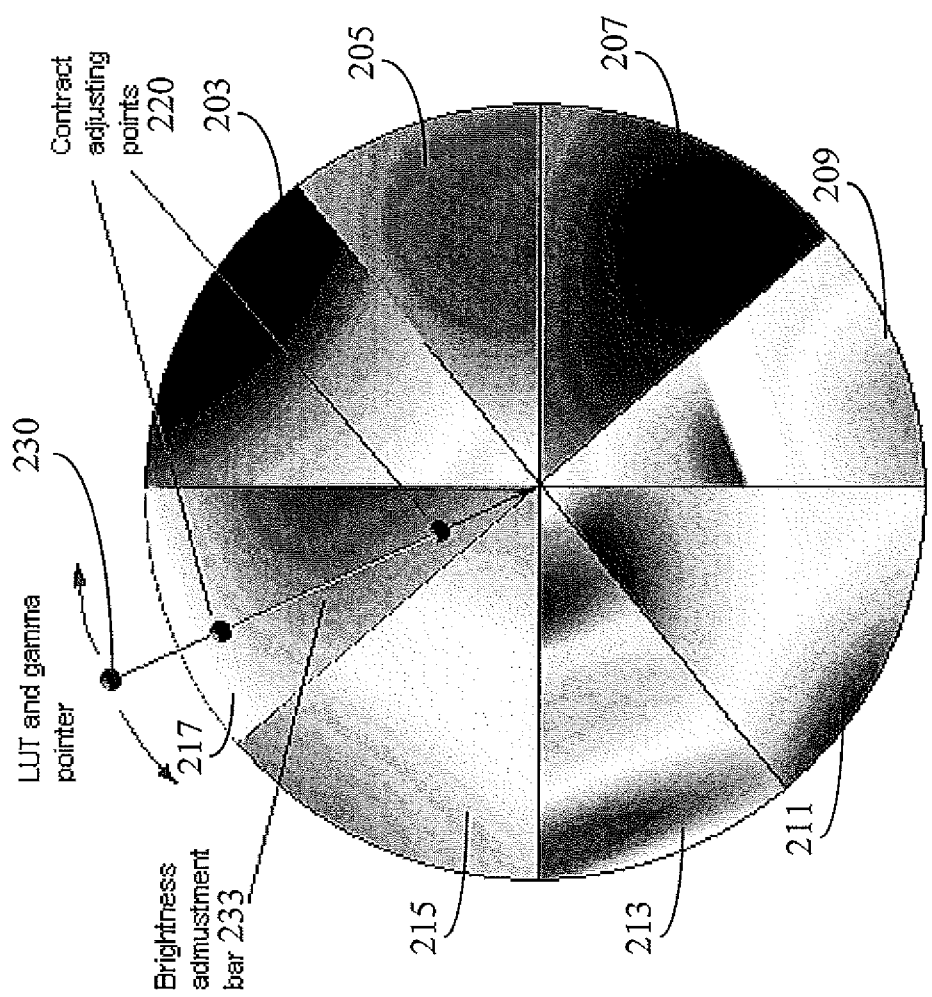
FIG. 2 shows an image parameter selection control comprising a Pinwheel Image Presentation Adjustment control displaying multiple color lookup tables in a pinwheel graph enabling a user to select a color lookup table, brightness, contrast, and gamma, according to invention principles.

FIGS. 2-14 show medical interface image parameter selection controls and associated features. Although FIGS. 2-14 are depicted in gray scale shading this is representative only. The gray scale shades represent color shades and gray scale shades in FIGS. 2-14. FIG. 2 shows image parameter selection control 36 (FIG. 1) comprising a Pinwheel Image Presentation Adjustment control displaying multiple predetermined user selectable color lookup tables in sectors 205, 207, 209, 211, 213, 215 and 217 (shown in gray scale in the Figures) and a grayscale shade lookup table in sector 203 in a pinwheel graph enabling a user to select a color or gray scale lookup table, brightness, contrast, gamma, and inverted state. A user drags lookup table and gamma pointer bar 233 by dragging outer pointer 230 using cursor device 26 (FIG. 1) to different sectors 203, 205, 207, 209, 211, 213, 215 and 217 to select a desired lookup table, for example. A color or gray scale gradient pattern in a sector is typically curved about the center of the pinwheel. Larger numbers of lookup tables result in a smaller pie sector area for individual lookup tables. Within a sector representing a color or grayscale lookup table, a user employs pointer bar 233 with adjustable points 220 for adjusting contrast, movable area between points 220 for adjusting brightness, and point 230 for adjusting gamma in the context of the selected color or grayscale lookup table within which bar 233 is located. In one embodiment adjustment bar 233 remains attached to the origin of the pinwheel and extends to at least the outside perimeter of the pinwheel and is adjusted in multiple different ways. In another embodiment, bar 233 is detached or detachable from the origin of the pinwheel.

FIG. 3 illustrates image parameter selection control legends including lookup table and gamma selection pointer 230, window top pointer 306, window bottom pointer 303, contrast and brightness control 309 (aligned along bar 233) between points 303 and 306.

Figure 11:
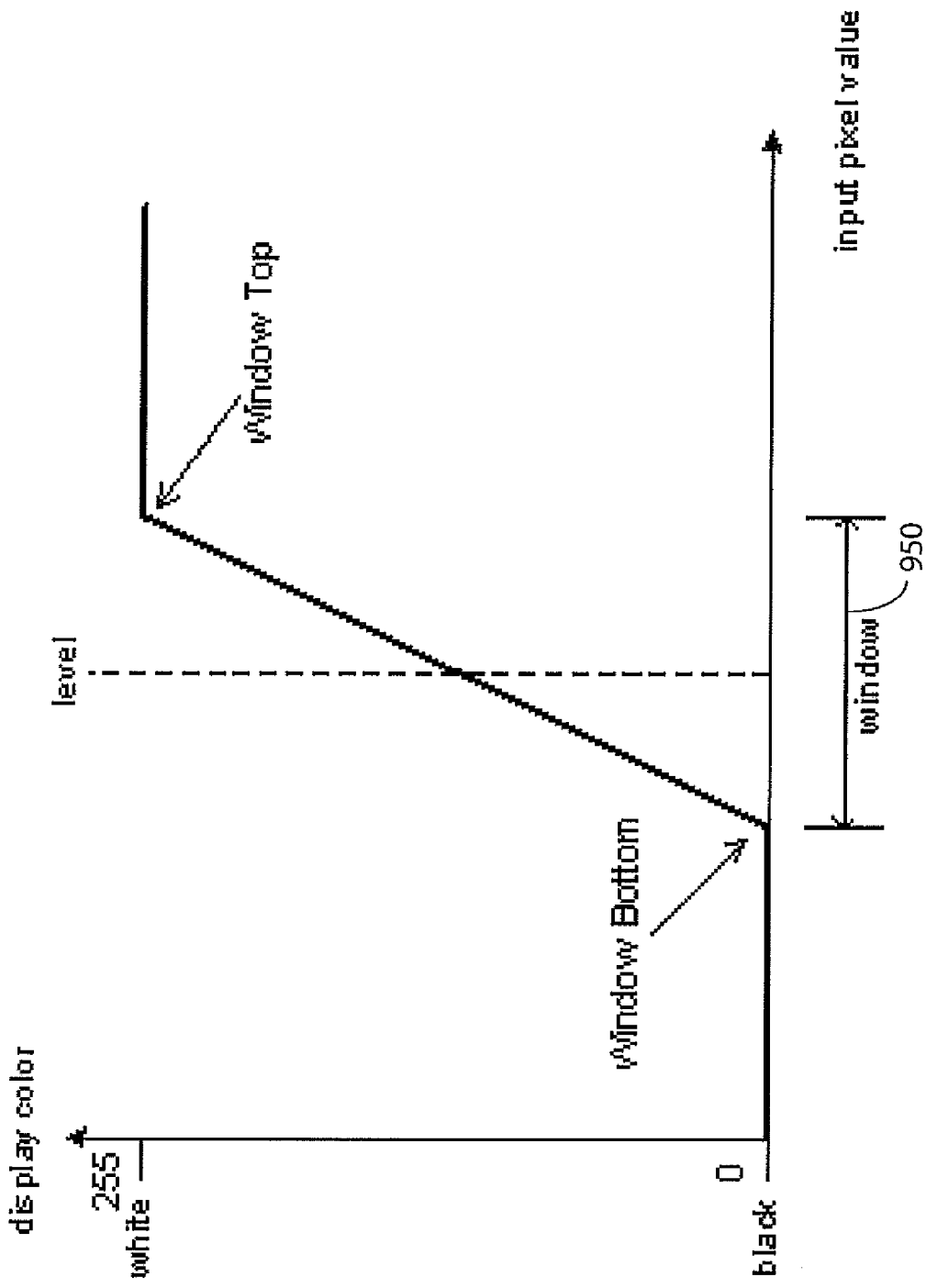
FIG. 11 shows a graph of brightness and contrast change over an adjustable window range of an image parameter selection control, according to invention principles.

FIG. 11 illustrates brightness and contrast change in a graph of gray scale or color (units 0-255 y-axis) against input pixel value (e.g. 0-255 x-axis) and showing an adjustable window range 950 selected using image parameter selection control 36 (FIG. 1). Window range 950 is set by selection of window top pointer 306 and window bottom pointer 303 on bar 233 (FIG. 3). Image contrast is an image property determining the degree to which an object is distinguishable from other objects and background. A user increases image contrast by moving window top and bottom pointers 306 and 303 apart and decreases contrast by moving window top and bottom pointers 306 and 303 towards each other. A user adjusts contrast by changing window width 950 (FIG. 11) by changing distance between points 306 and 303 on bar (linear element) 233 (FIG. 3). In one mode, a user successively selects points 303 and 306 using cursor device 26 and moves points 303 and 306 together toward or away from each other in a mirror fashion in response to dragging one of the selected pointers inward or outward along the control beam 233.

Brightness is an image property that determines the light intensity (luminance) of a digital image. A user reduces image brightness by moving the portion of bar 233 between bottom pointer 303 and top pointer 306 along bar 233 towards origin of the pinwheel which results in revealing lower pixel values. A user increases image brightness by moving the portion of bar 233 between bottom pointer 303 and top pointer 306 along bar 233 towards the periphery of the pinwheel which causes lower pixel values to fade into the background and reveals higher pixel values in an image. Pixel values greater than the window top pointer 306 value (as indicated in a graph such as FIG. 11), display as white. Pixel values less than the window bottom pointer 303 value (as indicated in a graph such as FIG. 11), display as black. The pinwheel image parameter selection control 36 presents pixel values as a percentage. The smallest value is represented as 0%, and the largest value is presented as 100%. In one mode a user selects and moves points 303 and 306 separately and individually along bar 233 and in a further mode a user moves both points in the same direction in response to dragging one of the points to adjust image brightness. In digital imaging, Luminance refers to black-and-white information and luminance correction is achieved by adjusting various attributes including brightness and contrast.

FIG. 9 illustrates adjusting brightness using image parameter selection control 36 (FIG. 1). A user changes image brightness by moving the portion of bar 233 between bottom pointer 303 and top pointer 306 (a Window also termed a Brightness Control) along bar 233. If both Top and Bottom pointers 306 and 303 are within the pinwheel range, they are moved together along bar 233 by a user dragging operation to change image brightness. In response to moving the Window outward, if top pointer 306 hits the pinwheel perimeter, the top pointer 306 position automatically remains at the edge of the pinwheel while the top and bottom pointer settings continue to change until the values reach a pre-determined value (e.g., 150%). Similarly, In response to moving the Window inward, if Bottom Pointer 303 reaches the pinwheel origin, Bottom Pointer 303 remains at the pinwheel origin while the top and bottom window levels continue to change until reaching a predetermined value (i.e. −50%). Annotation text (or a tooltip, depending on the tool area) shows corresponding window level values in response to a user placing a cursor next to pointer 306 or 303.

FIG. 4 illustrates changing a color lookup table using image parameter selection control 36 (FIG. 1). A user selects a different color (or gray scale) lookup table by dragging bar 233 via point 230 from a first lookup table of sector 403 to a different second lookup table of sector 405, for example.

FIG. 5 illustrates adjusting gamma using image parameter selection control 36 (FIG. 1). Gamma determines distribution of brightness within an intensity spectrum of a monitor, printer or scanner, for example. An ideal linear device would have a gamma of 1.0, whereas a monitor or printer may have a gamma value in the range of 1.8 to 2.6 in order to match the output more closely to the original image, for example. A user adjusts gamma factor in control 36 by using cursor device 26 to drag bar 233 via point 230 around the pinwheel perimeter within a lookup table sector. A user adjusts gamma within the range +2 to −2 by moving bar 233 between sector limits 503 and 505, for example. A positive gamma results in a brighter image display.

FIG. 6 illustrates adjusting image contrast by adjusting initial positions of bottom pointer 303 (shown as an initial value of 0%) and top pointer 306 (shown as an initial value of 100%) along bar 233 using image parameter selection control 36 (FIG. 1). A user adjusts the Window top and the Window bottom by moving Window Top Pointer 306 (set at 90% level) and Window Bottom Pointer 303 (set at 20% level), as illustrated in FIG. 7 to expand or shrink a color or gray scale gradient. These pointers travel along bar 233 in either direction of the bar, limited by the origin and the perimeter of the pinwheel.

FIG. 8 illustrates inverting a color lookup table using image parameter selection control 36 (FIG. 1). In order to invert a color lookup table, a user drags Window Top Pointer 306 to the other side of Window Bottom Pointer 303 on bar 233 or vise versa. In lookup tables that are not capable of inversion (i.e. lookup tables other than color or gray scale tables), the crossing of pointers 306 and 303 feature is disabled. In another embodiment, inversion of a lookup table is achieved by adding a user selectable Inverted lookup table in a sector in the image parameter selection control 36 pinwheel.

FIG. 10 illustrates enlarging (zooming) a color lookup table sector of image parameter selection control 36. System 10 enables a user to enlarge selected lookup table sector 656 area by double-clicking, for example, in the selected sector area to provide enlarged sector 653. In this zoom-in view, the remainder of the image parameter selection control 36 pinwheel becomes dim except for selected lookup table 653 and enlarged selected sector 653 is displayed in the foreground, overlapping the entire pinwheel area, to allow adjustment. In response to a user double-clicking, the pinwheel in the zoom-in mode, the pinwheel reverts to the original view.

Figure 14:
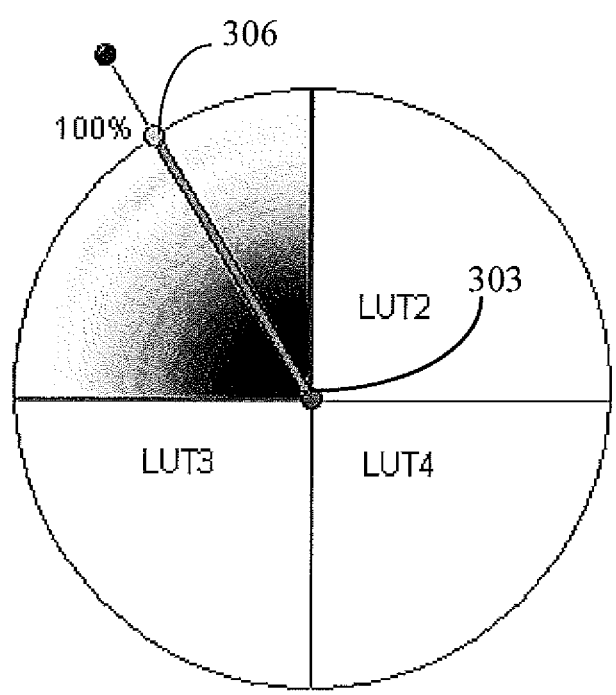
FIG. 14 illustrates a gray scale lookup table of an image parameter selection control, according to invention principles.

FIGS. 12 and 13 show an embodiment in which image parameter selection control 36 comprises vertical color lookup tables instead of circular shape based color lookup tables. Specifically, FIG. 12 shows a group of color and grayscale lookup tables (shown as gray scale tables for simplicity) having window top value 705 and window bottom value 703 representing 100% and 0% window values respectively. FIG. 13 illustrates adjusting window top and bottom values of a lookup table. Specifically, FIG. 13 shows an adjusted window top value 715 (85%) and window bottom value 713 (15%) within lookup table 720, for example FIG. 14 illustrates a gray scale lookup table in image parameter selection control 36 (FIG. 1). Window top value 306 is set at 100% and window bottom value 303 is set at 0% within the gray scale lookup table.

Figure 15:
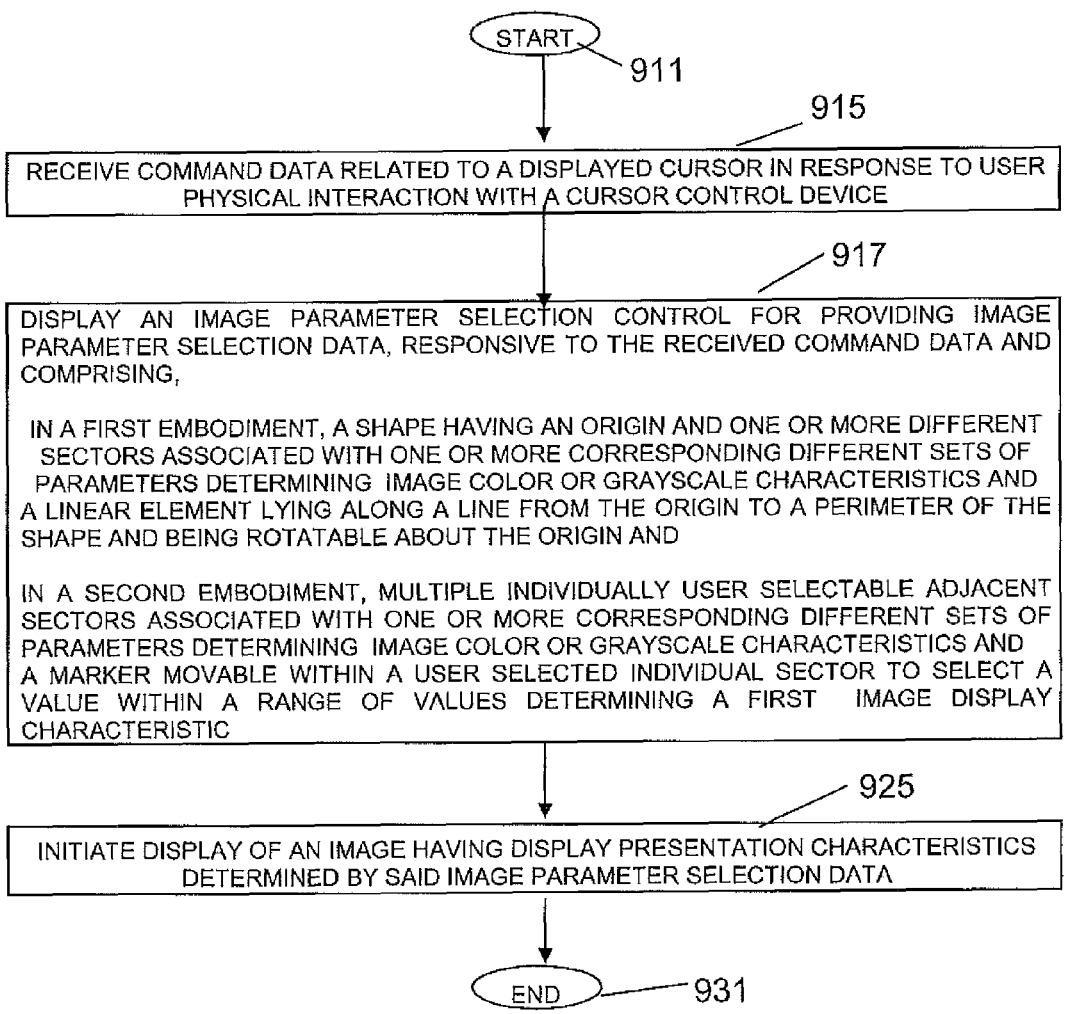
FIG. 15 shows a flowchart of a process employed by a user interface system for determining image display presentation characteristics, according to invention principles.

FIG. 15 shows a flowchart of a process employed by user interface system 10 (FIG. 1) for determining display presentation characteristics of a medical image, for example. In step 915 following the start at step 911, user interface (cursor control) device 26 receives command data related to a displayed cursor in response to user physical interaction with the device. In step 917, display 19 in a first embodiment (e.g., as shown in FIG. 2) displays image parameter selection control 36 for providing image parameter selection data, responsive to the received command data and comprising, a shape having an origin and one or more different sectors associated with one or more corresponding different sets of parameters determining image color or grayscale characteristics and a linear element. The shape substantially comprises at least one of, a two dimensional circle, a three dimensional sphere, another three dimensional shape, a square, an ellipse, a rectangle and a cube.

The linear element lies along a line from the origin to a perimeter of the shape and is rotatable about the origin, (a) within a sector to select a value within a range of values determining a first image display characteristic and (b) between sectors to select one of the different sets of parameters determining image color or grayscale characteristics. The first image display characteristic comprises luminance or a function of luminance such as gamma and the characteristic value comprises a gamma determining value, a brightness determining value and a contrast determining value. The linear element includes first and second different markers movable by a user along the linear element to overlay and select points in a sector representing parameter values determining an image color or grayscale characteristic, the selected values determining a maximum and minimum characteristic value. The first and second different markers represent a range of the characteristic value between the maximum and minimum characteristic value and the range is inverted in response to reversing relative position of the first and second markers on the linear element.

In a second embodiment (e.g., as shown in FIG. 12) display 19 displays image parameter selection control 36 providing image parameter selection data, responsive to the received command data and comprising, multiple individually user selectable adjacent sectors associated with one or more corresponding different sets of parameters determining image color or grayscale characteristics and one or more markers. The multiple individually user selectable adjacent sectors are parallel and individually have a shape comprising at least one of, a rectangle or a bar. The markers are movable within a user selected individual sector to select values within a range of values determining image display characteristics. A marker is movable to select a point in a sector representing a parameter value determining an image luminance, the selected value determining a maximum or minimum characteristic value. In step 925 display processor 36 initiates display of an image having display presentation characteristics determined by the image parameter selection data. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system, image controls and processes of FIGS. 1-15 are not exclusive. Other systems, processes and image controls may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system advantageously combines image presentation parameters in a pinwheel (or other shape e.g. ellipse, square, rectangle) graphical element and employs a control bar for changing gamma, color or gray scale lookup table, image contrast and brightness and enables inversion of a lookup table by swapping window top and bottom values. Further, the processes and applications may, in alternative embodiments, be located on one or more (e.g., distributed) processing devices on a network linking the units of FIG. 1. Any of the functions, image controls and steps provided in FIGS. 1-15 may be implemented in hardware, software or a combination of both.

What is claimed is:

1. A user interface system for determining image display presentation characteristics, comprising:
    a cursor control device for receiving command data related to a displayed cursor in response to user physical interaction with the device;
    a displayed image parameter selection control for providing image parameter selection data, responsive to the received command data and comprising,
        a shape having an origin and one or more different sectors associated with one or more corresponding different sets of parameters determining image color or grayscale characteristics and
        a linear element lying along a line from said origin to a perimeter of said shape and being rotatable about said origin,
            (a) within a sector to select at least one value within a corresponding range of values determining a group of image display characteristics and
            (b) between sectors to select one of said different sets of parameters determining image color or grayscale characteristics; and
    a display processor for initiating display of an image having display presentation characteristics determined by said image parameter selection data.

2. A system according to claim 1, wherein
said image is a medical image and
said image display characteristics comprise luminance or a function of luminance.

3. A system according to claim 2, wherein
said function of luminance comprises gamma.

4. A system according to claim 1, wherein
said linear element includes at least one marker movable by a user along the linear element to overlay and select a point in a sector representing a parameter value determining an image luminance, the selected parameter value determining a maximum or minimum characteristic value.

5. A system according to claim 4, wherein
said characteristic value comprises a gamma determining value.

6. A system according to claim 4, wherein
said characteristic value comprises at least one of, (a) a brightness determining value and (b) a contrast determining value.

7. A system according to claim 1, wherein
said shape substantially comprises a two dimensional circle.

8. A system according to claim 1, wherein
said shape substantially comprises a three dimensional sphere.

9. A system according to claim 1, wherein
said shape is three dimensional.

10. A system according to claim 1, wherein
said shape substantially comprises at least one of, (a) a square, (b) an ellipse, (c) a rectangle and (d) a cube.

11. A system according to claim 1, wherein
said linear element includes first and second different markers movable by a user along the linear element to overlay and select points in a sector representing parameter values determining a image color or grayscale characteristic, the selected values determining a maximum and minimum characteristic value.

12. A system according to claim 11, wherein
said first and second different markers represent a range of said characteristic value between said maximum and minimum characteristic value and said range is inverted in response to reversing relative position of said first and second markers on said linear element.

13. A user interface system for determining image display presentation characteristics, comprising:
- a cursor control device for receiving command data related to a displayed cursor in response to user physical interaction with the device;
- a displayed image parameter selection control for providing image parameter selection data, responsive to the received command data and comprising,
  - a plurality of individually user selectable adjacent sectors associated with one or more corresponding different sets of parameters determining image color or grayscale characteristics and
  - a marker movable within a user selected individual sector to select a value within a range of values determining a first image display characteristic; and
- a display processor for initiating display of an image having display presentation characteristics determined by said image parameter selection data.

14. A system according to claim 13, wherein
said plurality of individually user selectable adjacent sectors are parallel and individually have a shape comprising at least one of, a rectangle or a bar.

15. A system according to claim 13, wherein
said image is a medical image and
said first image display characteristic comprises luminance or a function of luminance.

16. A system according to claim 15, wherein
said function of luminance comprises gamma.

17. A system according to claim 13, wherein
said marker is movable to select a point in a sector representing a parameter value determining an image luminance, the selected value determining a maximum or minimum characteristic value.

18. A system according to claim 17, wherein
said characteristic value comprises a gamma determining value.

19. A system according to claim 17, wherein
said characteristic value comprises at least one of, (a) a brightness determining value and (b) a contrast determining value.

20. A method employed within a user interface system for determining image display presentation characteristics, comprising the activities of:
- receiving command data related to a displayed cursor in response to user physical interaction with the device;
- displaying an image parameter selection control for providing image parameter selection data, responsive to the received command data and comprising,
  - a shape having an origin and one or more different sectors associated with one or more corresponding different sets of parameters determining image color or grayscale characteristics and
  - a linear element lying along a line from said origin to a perimeter of said shape and being rotatable about said origin,
    - (a) within a sector to select a value within a range of values determining a first image display characteristic and
    - (b) between sectors to select one of said different sets of parameters determining image color or grayscale characteristics; and
- initiating display of an image having display presentation characteristics determined by said image parameter selection data.

\* \* \* \* \*